(12) United States Patent
Carrero Villarroel et al.

(10) Patent No.: US 12,734,016 B2
(45) Date of Patent: Sep. 15, 2026

(54) METHOD FOR MANUFACTURING A SPLINT OR SURGICAL GUIDE FOR THE IMPLANTATION OF AT LEAST ONE DENTAL IMPLANT

(71) Applicant: TECH XIKA PTT, S.L., Lleida (ES)

(72) Inventors: Xavier Carrero Villarroel, Lleida (ES); Sebastian Sassi Diaz, Lleida (ES)

(73) Assignee: TECH XIKA PTT, S.L., Lleida (ES)

( * ) Notice: Subject to any disclaimer, the term of this patent is extended or adjusted under 35 U.S.C. 154(b) by 60 days.

(21) Appl. No.: 18/834,822

(22) PCT Filed: Feb. 1, 2022

(86) PCT No.: PCT/ES2022/070050
§ 371 (c)(1),
(2) Date: Jul. 31, 2024

(87) PCT Pub. No.: WO2023/148410
PCT Pub. Date: Aug. 10, 2023

(65) Prior Publication Data

US 2025/0221793 A1 Jul. 10, 2025

(51) Int. Cl.
*A61B 34/10* (2016.01)
*A61C 1/08* (2006.01)

(52) U.S. Cl.
CPC .............. *A61C 1/084* (2013.01); *A61B 34/10* (2016.02); *A61B 2034/101* (2016.02)

(58) Field of Classification Search
None
See application file for complete search history.

(56) References Cited

U.S. PATENT DOCUMENTS

| | | | | |
|---|---|---|---|---|
| 5,320,529 A | 6/1994 | Pompa | | |
| 2011/0275032 A1* | 11/2011 | Tardieu | A61C 8/0089 | 433/76 |
| 2013/0309628 A1* | 11/2013 | Orth | A61C 1/084 | 433/173 |
| 2014/0203463 A1 | 7/2014 | Haber | | |
| 2018/0140392 A1 | 5/2018 | Wismeijer | | |

FOREIGN PATENT DOCUMENTS

WO 2010/125593 A1 11/2010

OTHER PUBLICATIONS

International Search Report for PCT/ES2022/070050 dated Sep. 9, 2022.
Written Opinion for PCT/ES2022/070050 dated Sep. 9, 2022.
International Preliminary Report on Patentability for PCT/ES2022/070050 dated May 6, 2024.

* cited by examiner

*Primary Examiner* — Eileen M Adams
(74) *Attorney, Agent, or Firm* — Sughrue Mion, PLLC

(57) ABSTRACT

A method for manufacturing a splint or surgical guide for the implantation of at least one dental implant, relating to a part of a guided oral surgery process by which at least one implant is placed or implanted in a patient's jaw to replace the function of one or more natural teeth. The manufacturing method is implemented by a computer program. The object is to improve the implant placement process in an optimal and minimally invasive, as well as more simplified way.

4 Claims, 4 Drawing Sheets

22
4
50
22
4
21
3
21
22
3
4

METHOD FOR MANUFACTURING A SPLINT OR SURGICAL GUIDE FOR THE IMPLANTATION OF AT LEAST ONE DENTAL IMPLANT

CROSS REFERENCE TO RELATED APPLICATIONS

This application is a National Stage of International Application No. PCT/ES2022/070050 filed Feb. 1, 2022.

OBJECT OF THE INVENTION

The present invention, method for manufacturing a splint or surgical guide for the implantation of at least one dental implant, relates to a part of a guided oral surgery process by which at least one implant is placed or implanted in a patient's jaw to replace the function of one or more natural teeth. The manufacturing method is implemented by a computer program. The object of the invention is to improve the implant placement process in an optimal and minimally invasive, as well as more simplified way.

The present invention belongs to the field of dental implantology and in particular to the dental implant placement process.

BACKGROUND OF THE INVENTION

Currently, dental implantology techniques make it possible to replace dental roots by means of dental implants made of biocompatible material, usually made of a titanium alloy, to which the corresponding prostheses or artificial teeth are in turn attached.

The phases of implanting said implants are usually summarised as:

- an initial phase of inserting the implant,
- a subsequent intermediate phase of osseointegration which involves a waiting time, and
- a final phase of fixing the definitive prosthesis.

Currently, oral implantology has progressed significantly in recent years with the appearance on the market of software systems or computer programs that make it possible to virtually design implant planning and transfer this information to the surgical field.

Computer-guided surgery is a technique that allows implants to be placed in the exact location that has been previously planned with the help of a computer and 3D technology.

This technique starts with the digitisation of the anatomy of a patient's oral cavity and, via an intraoral scanner and computed tomography, 3D images are obtained using CBCT (Cone Beam Computed Tomography) of the patient's entire dental structure, obtaining the patient's digital oral model. From this information, the previous digitisation is imported into a planning software or computer program. From the digital oral model, an expert in implantology determines the types of implants to be implemented, the diameter thereof, the height thereof and the location of the heads thereof in the digital oral model. Thus, the images of the digitalisation and the study by the expert in implantology are aligned to achieve good planning in the placement of the implants.

Based on the previously obtained information, a virtual surgical guide or splint is designed with the help of the software or computer program. Said guide is used to subsequently perform surgery on the patient using a surgery kit that comprises milling tools with different lengths, carriers, extractors, as well as other components that are necessary for the surgery. From the virtual design of the guide or splint, a digital file is generated for the subsequent manufacture of the guide or splint through a 3D printing or milling process. Said surgical guide or splint incorporates the holes through which the elements for implanting the implant will be inserted, mainly: the milling tools to machine the channels in the jaws where the implants will be subsequently implanted, the carriers, and the implants themselves. Said holes in the guide or splint can incorporate rings that guide both the placement of the implants in the positions that have been previously planned and the milling tools for the machining thereof. Said rings are placed in the holes of the guide or splint after manufacture thereof.

This splint or surgical guide, which is used by an expert in implantology or implantologist on the day of the operation, avoids having to open the gum as is done in traditional surgery. Likewise, the guide or splint allows the surgeon to drill only to the necessary depth, thanks to the carriers, milling tools or milling cutters and rings that have the necessary stops so as not to exceed the depth planned by the computer program and the implantologist, thus avoiding the risk of affecting any important anatomical structure.

There are several variables on which the final position of an implant depends, for example, parameters such as the effective milling length, inactive milling length, ring height, and length or height of the implant, which can be placed with the head of the implant (end joining the attachment or closer to the dental prosthesis) at the level of the jawbone, or below the bone level or even above the bone level.

This surgical technique has notable advantages over traditional implant placement surgery.

On the other hand, current guided surgery protocols are designed to place implants exclusively at bone level and require the use of a milling cutter or milling tool for implants that have one same diameter and different heights or lengths.

DESCRIPTION OF THE INVENTION

The present invention relates to a method for manufacturing a splint/surgical guide.

Specifically, the method for manufacturing a splint or surgical guide for the implantation of at least one dental implant in a patient, and more specifically in at least one jaw of a patient, comprises:

- Obtaining, by means of a scanning system and a computed tomography system, at least one three-dimensional image of a patient's oral cavity, to generate a digital oral model,
- Determining the features of the dental implant to be implanted, including the type, height and diameter of the dental implant, as well as the location of the head of the at least said dental implant in the digital oral model,
- Generating, based on the type and location of the at least one dental implant, a virtual surgical plan, which includes, at least:
  - Creating a digital design of a surgical guide or splint comprising at least one hole with a guide and stop ring located at a first distance from the location of the head of the implant in the digital oral model,
  - Choosing at least one milling tool to be inserted into the hole of the splint, with a diameter suitable for the diameter of the implant, an inactive length with a washer or protrusion to come in contact with the guide and stop ring, and a useful machining length ending at a free end, with the useful machining length being greater than the height of the implant and the distance between the washer or protrusion, and the free end of the useful length is equal to the sum of the first distance and the height of the implant, Determining the milling sequence by using the at least said milling tool for machining the implant insertion channel in a jaw of the digital oral model, and Manufacturing the splint or surgical guide based on the digital design thereof.

Another optional step of the method of the invention after choosing the milling sequence, is determining a carrier with a specific diameter for the insertion thereof and the insertion of the implant into the hole of the splint and its subsequent fastening in the implant insertion channel. Said carrier has a length greater than the first distance between the ring of the splint and the head of the implant, but it allows the implant to be placed in its location and at that specific distance, even below the bone, thanks to its end joining the implant with a diameter equal to or less than that of the head of the implant.

Preferably, the surgical guide or splint comprises at least two holes with a ring in each of them, the rings being at two different first distances for the positioning of at least two implants with the same diameter. Likewise, the milling tool for machining the at least two channels is the same.

After manufacturing the splint or surgical guide by 3D printing or milling adapted to the patient's oral model and previous plan, incorporating the at least one hole, the ring, preferably made of titanium, is then inserted into the aforementioned hole, which will act as guide and stop when the milling cutter and carrier are inserted into the hole of the splint or surgical guide. The ring is preferably inserted by means of a tool at the end of which the ring is inserted and subsequently the ring is inserted into the hole of the splint by pressing with the tool.

The material of the splint or surgical guide is preferably a biocompatible resin when it is manufactured by 3D printing and preferably a biocompatible acrylic polymer when it is manufactured by milling, more preferably polymethylmethacrylate (PMMA). In either case, other biocompatible materials suitable for the manufacture of splints or dental surgical guides may be used.

The method of the present invention is part of a guided surgery process in dental implantology which allows the implant to be positioned at different levels, not only at bone level as occurs in the state of the art. This manufacturing method should be considered whenever it is necessary that the milling cutter to be used be guided by the ring at all times during the machining of the implant channel. Creating the implant implantation channel usually requires machining of the same by more than one milling tool, acting sequentially, such that the channel is formed by the consecutive machining of the channel by milling cutters that progressively increase the diameter and length thereof until finally inserting the milling cutter with the diameter suitable for subsequently inserting the implant until the head of the implant is placed in the planned location.

The method requires that, when determining the surgical plan for positioning the implant, the position of the head of the implant is planned in the digital oral model, to subsequently determine the positioning of the stop ring in the splint or guide at a first distance or offset, this being the distance that exists from the head of the implant location to the ring located in the access hole of the surgical guide or splint. As mentioned, said ring determines the insertion stop in the hole of the guide or splint of the milling tool or milling cutter, as well as the insertion stop in the hole of the guide or splint of the carrier used to insert the implant into the channel previously machined in the bone by the sequence of milling tools or milling cutters.

Both the milling cutter and the carrier incorporate a washer or protrusion that abuts against the ring of the splint, determining the correct position of the milling cutter and the carrier with respect to the location of the implant.

The milling tool or milling cutter comprises three zones: a first zone or coupling length for fastening the milling tool to a tool that applies torque to it, followed by a second zone or inactive length that has a section that cannot be machined and is separated from the first zone by the stop washer that makes contact with the ring of the splint during insertion of the milling cutter into the hole of said splint, and a third zone or useful machining length, following the inactive length and which ends at a free end that has the working and/or milling section of the milling cutter, responsible for machining the implant introduction channel in the jawbone.

The distance between the washer or protrusion of the milling tool and the free end of the useful machining length must be equal to the sum of the first distance, between the location of the head of the implant and the ring of the splint or surgical guide, and the height of the implant, i.e., the length of the implant.

Based on the foregoing, it is possible to use a single milling tool or milling cutters to machine different channels in the bone for the placement of implants with the same diameter and different heights, by varying the first distance between the location of the head of the implant and the position of the ring in the splint or guide. Specifically, the position of the part of the ring closest to the surface of the splint, which is where the washers or protrusions of the milling cutter and carrier will abut.

Thus, by increasing or decreasing the first distance, varying the height of the splint or surgical guide depending on the location of the head of the implant, the same milling cutter can be used to machine different implant channels with the same diameter.

The carrier is an element to which the implant is joined at a first end, and after inserting said first end with the implant into the hole of the splint up to the washer of the carrier, at the end opposite to the one joining the implant, it abuts the ring of the splint after having applied tightening torque to the carrier. Said tightening torque for inserting the implant into the bone is applied to the carrier above the washer by means of a tightening tool or ratchet.

Current guided surgery protocols are designed to place implants exclusively at the jawbone level. The method object of the invention allows not only placing the implants at bone level, but also below the bone level, embedded therein, an increasingly common practice in the placement of dental implants, or even above the bone level. This is possible because the lower end of the carrier has a smaller diameter than the diameter of the head of the implant, thus becoming an extension of the implant which allows it to be inserted into the bone and therefore the implant can be inserted and placed below the bone level when necessary.

The guide or splint designed and manufactured according to the previous method allows one same milling cutter to be used for different implant positions, bone level or below the bone, and different implant heights. This is achieved in the planning with the computer program or planning software, where the necessary height for each case is programmed, by means of the guide or splint with the ring that is manufactured after planning and with the suitable carriers having different heights, to perform the work.

As an alternative to milling tools or milling cutters, drill bits could be used.

A second object of the invention is a computer program product, specifically, a computer program product which includes code instructions that, once executed in a computer system or computer, carry out the method described above.

BRIEF DESCRIPTION OF THE DRAWINGS

To complete the description of the present invention and to make the features of the invention more readily understandable, a set of figures is attached by way of illustration and not limitation.

PREFERRED EMBODIMENT OF THE INVENTION

Next, with reference to the previous figures, a description of a preferred embodiment of the invention is provided.

This manufacturing method, as part of a guided surgery process in dental implantology, is integrated into the planning phase of said surgery, specifically until the manufacture of a surgical guide or splint 4 that will subsequently be used in the surgery to be performed on the patient.

Figure 1:
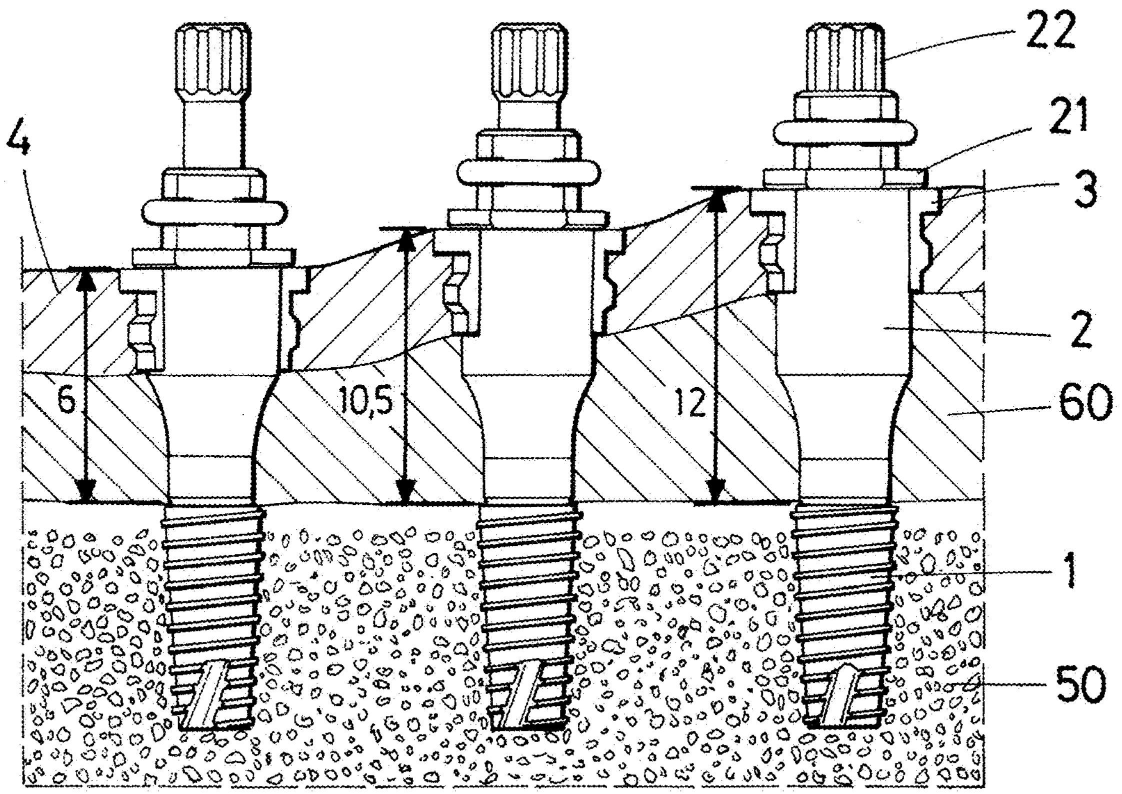
FIG. 1 shows different implants placed at bone level.

Current guided surgery protocols are designed to place implants 1 exclusively at the jawbone level, as shown in FIG. 1. Said protocols include the manufacture of a splint for guiding the milling tool in the placement of the implant 1. Specifically, FIG. 1 shows three examples of different implants at different depths with respect to the gum 60, which varies in height, but is at the same depth with respect to the bone level 50. The examples represent three identical implants 1 that require different carriers 2 for their placement as well as different milling lengths for the machining of each of the channels wherein the implants 1 are inserted.

Figure 2:
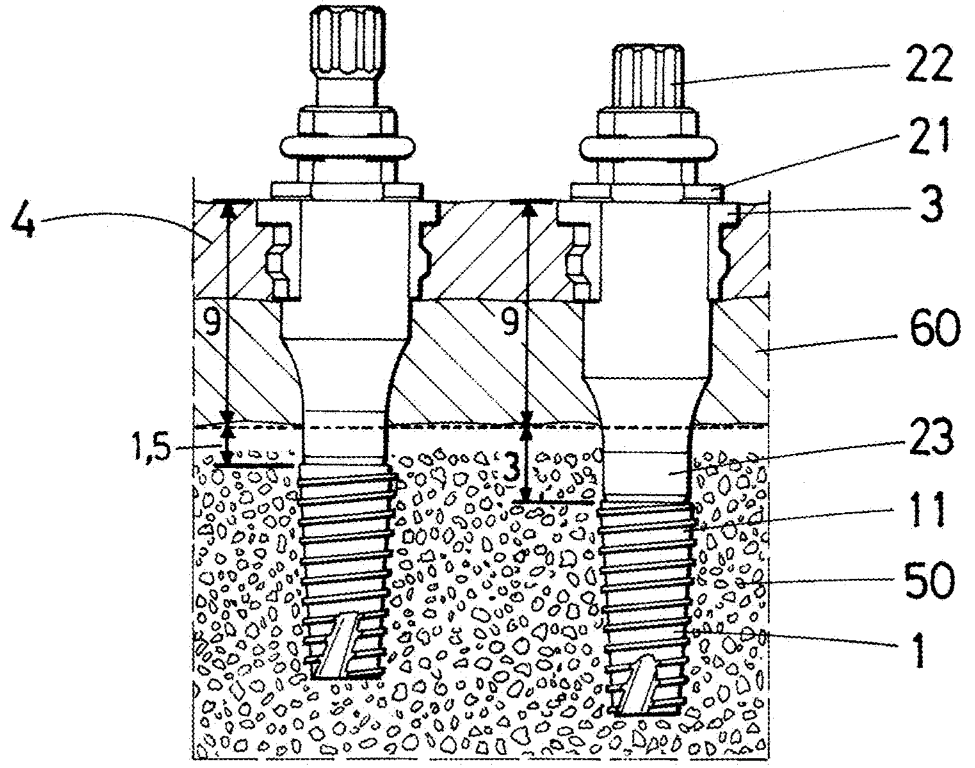
FIG. 2 shows different implants placed at different levels, not just bone level, for solutions according to the method of the present invention.

The method object of the invention allows not only placing the implants at bone level, but also below the bone level, embedded therein, an increasingly common practice in the placement of dental implants, or even above the bone level. FIG. 2 shows two implants 1 located at different depths with respect to the bone level (50) but with a gum (60) of the same height. This is possible thanks to the use of the carrier (2) that has its end joining the implant 1 with a diameter equal to or less than the diameter of the head 11 of the implant 1.

According to the method of the present invention, a step of obtaining, by means of a scanning system and a computed tomography system, at least one three-dimensional image of a patient's oral cavity is first carried out with known means, to generate a digital oral model. The patient's data is recorded by scanning and CBCT tomography (obtaining DICOM files), in three dimensions and acquired from the oral cavity, to import them into a planning software or computer program from the digital files obtained, in which the images obtained by the scanner and the tomograph will be aligned to have all the necessary information and guarantee a perfect match between the various data sources.

After the first step of acquiring the patient's data and generating their digital oral model, the implantologist or dental expert must carry out a comprehensive dental diagnosis or examination of the patient to determine the features of the implant or implants 1 to be placed in the patient. To do this, the implantologist must determine, in view of the digital oral model and with the help of the planning software or computer program, the features of the dental implant 1 to be implanted, including the type of dental implant 1, the height or length thereof, the diameter thereof, as well as the location of the head 11 of the at least one said dental implant 1 in the digital oral model. The dental implant 1 has a height or length determined by a first end or head 11 of the implant and a second end or base 12 of the implant. The head 11 of the implant is the area joining the implant 1 to the dental attachment, i.e., the area of the implant 1 closest to the dental prosthesis or area closest to the surface and through which the screw is inserted to retain the prothesis on the implant. At the second end 12 is the area of the implant 1 furthest from the surface.

The implantologist therefore determines, in view of the digital oral model, the number of implants 1 required by the patient, the location or position of the same and the corresponding type of restoration.

Based on the previous information provided by the implantologist along with the information obtained from the digital oral model such as, for example, the quality, width, height of the bone, etc., and the combined action of the planning computer program, accurate virtual planning of the surgery is achieved.

Therefore, in the planning computer program the implantologist defines where he or she wants to virtually position the implant, determining its height, diameter and angulation based on the information previously gathered from the scan and tomography. The computer program or software, with the foregoing information and along with the information libraries, provides the information needed to meet this objective defined by the implantologist. The implantologist is responsible for verifying and supervising the planning process and validating the surgical plan.

At this time, according to the invention and based on the type and location of the at least one dental implant 1, a virtual surgical plan is generated for the manufacture of a surgical guide or splint 4. The libraries of the planning computer program intervene in the generation of this plan and contain the information needed to complete the planning and, in particular, the determination of the location or final position of the implant 1, specifically of the head 11 of the implant 1, and the first distance or offset X between the head 11 of the implant 1 and the ring 3 arranged in the surgical guide or splint 4.

The generation of said virtual surgical plan comprises, at least, the creation of a digital design of a surgical guide or splint 4 (see FIG. 4) comprising at least one hole 45 with a ring 3 located at a first distance X from the head 11 of implant 1 in the digital oral model.

Said plan includes determining at least one milling tool 40 that has a diameter suitable for the diameter of the implant 1 and has a machining length or useful machining length 41 that is greater than or equal to the height of the implant 1, thus allowing channels 13 to be machined for the insertion of implants 1 of different heights with the same milling tool. This is achieved by adjusting the first distance X, between the head 11 of the implant 1 and the ring 4, so that by increasing this first distance X, the machining distance of the milling cutter is reduced.

Likewise, the surgical plan determines the sequence of use of the at least said milling tool 40 for machining the channel 13 for insertion of the implant 1 into a jaw 50 of the digital oral model.

The method also includes determining the carrier 2 that must be used for placing the implant 1 in its channel.

Once the surgical plan and the features of the digital splint or surgical guide 4 have been determined, the same is then manufactured either by 3D printing or by milling. Once said guide or splint 4 has been manufactured, the rings 3 are inserted into the hole 45 or holes using suitable tools.

Figure 3:
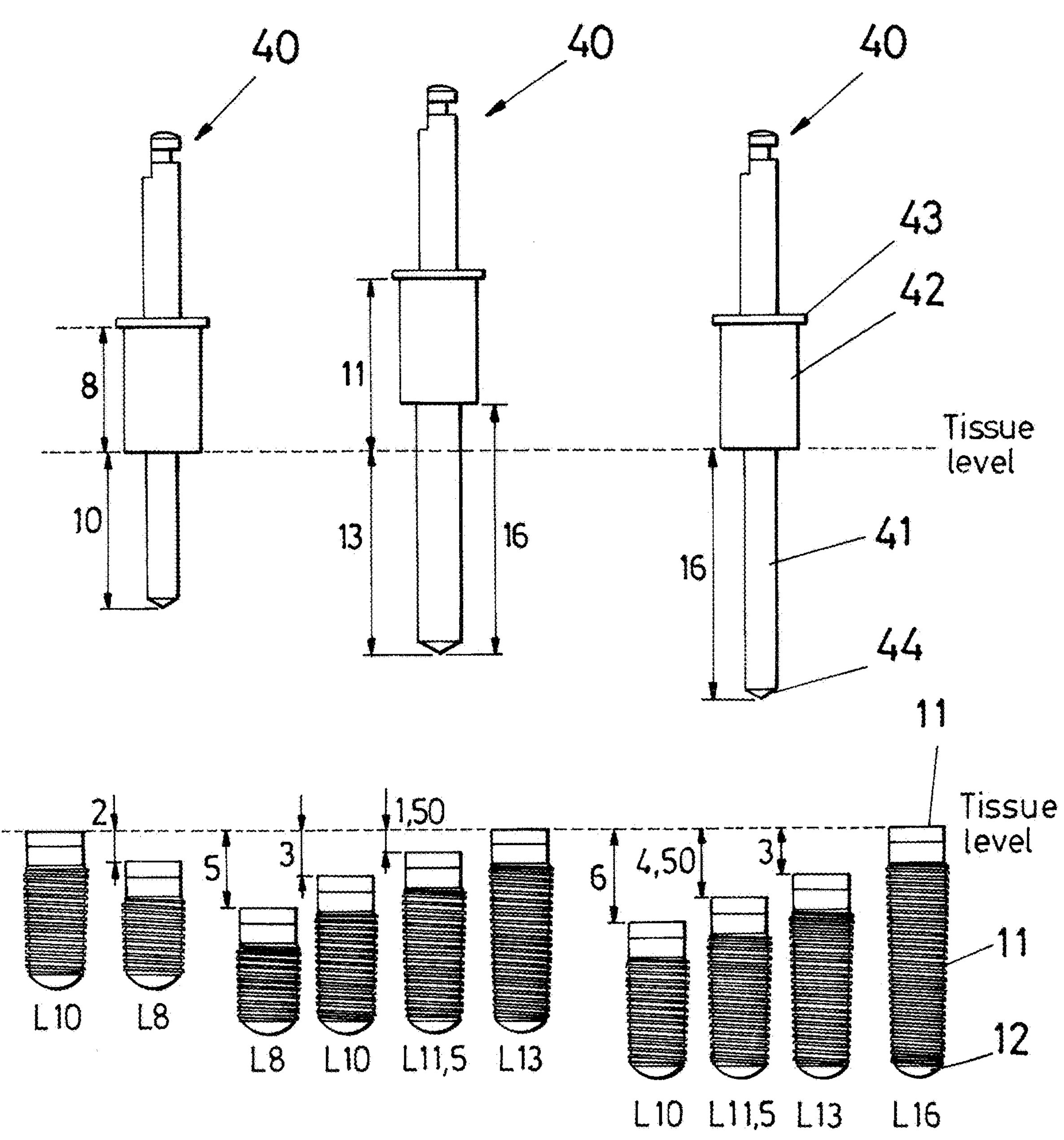
FIG. 3 shows different possibilities for implant placement in different locations at or below tissue level, usually the gums.

FIG. 3 shows three different milling tools or milling cutters 40 in the upper portion of the figure with which channels can be made to place implants at different depths with respect to the bone level.

For example, the same milling tool on the right, with a useful machining length 41 of 10 mm, can be used to machine the channel of an implant with height 10 arranged at tissue level or gum level or of an implant with height 8 arranged 2 mm below the gum level, both with the same diameter. The milling tool has an inactive length 42, i.e., a length not used for milling, unlike the useful length 41, which is inserted into the hole 45 of the splint or surgical guide 4 and which will stop as it is inserted into the hole 45 of the splint 4 when the washer 43 comes in contact with the ring 3 of the splint 4, leaving the ring 3 at a distance of 8 mm from the bone level. In the first milling cutter, the length of said inactive length 42 is 8 mm. In the example on the left, the first distance X, according to the invention, between the head 11 of the implant and the ring 3 is 8 mm, and in the example on the right, the first distance X, according to the invention, is 10 mm. Thus, the distance between the washer or protrusion 43 of the milling tool 40 and the free end 44 of the useful machining length 41 is equal to the sum of the first distance X, between the location of the head 11 of the implant 1 and the ring 3 of the splint or surgical guide 4, and the height of the implant 1, i.e., the length of the implant 1.

The milling cutter in the centre, with a useful length 41 of 16 mm, is used to machine the channels for implants 1 with lengths of 8, 10, 11.5 and 13 mm, arranged respectively at 5, 3, 1.5 and 0 mm from the gum level, all with the same diameter. In this example, however, despite the fact that the useful length 41 of the milling cutter is 16 mm, they are only used for machining channels of a maximum of 13 mm, so that the remaining 3 mm of the useful length 41 are not machined and they remain inside the splint 4 since the ring 3 is kept 11 mm from the level of the gum bone. In this example, the inactive length 42 of the milling cutter is also 8 mm, with the first distances X in each of the four examples being 16 mm, 14 mm, 12.5 mm and 11 mm, respectively from left to right. As in the previous case, the distance between the washer or protrusion 43 of the milling tool 40 and the free end 44 of the useful machining length 41 is equal to the sum of the first distance X and the height of the implant 1.

The milling cutter on the left in the figure, with a useful machining length 41 of 16 mm and an inactive length 42 of 8 mm, can be used to machine the channels of, for example, four implants of different heights and the same diameter, specifically with a height of 10, 11.5, 13 and 16 mm from left to right. These implants are located, also from left to right, at 6, 4.5, 3 and 0 mm from the gum level. In these examples, the first distance X, between the head 11 of the implant 1 and the ring 3 on the splint 4, is 14, 12.5, 11 and 8 mm respectively, in other words, the distance between the washer or protrusion 43 of the milling tool 40 and the free end 44 of the useful machining length 41 is equal to the sum of the first distance X and the height of the implant 1.

This method allows a milling cutter 40 with a specific useful machining length to be used for machining implant placement channels of different heights and the same diameter, reducing the number of tools to be used in the subsequent surgical method.

Thus, the ring 3 will be positioned at a height in the splint or guide 4 determining the first distance X next to the head 11 of the implant 1, and by varying said distance it is possible to adjust the distance of use of the useful machining length 41 of the milling cutter.

After the previous steps, and once each virtual implant has been correctly positioned, the computer program or software allows the surgical guide or splint to be manufactured with the specific positioning of each guide ring. The computer program or software will provide a print file for the 3D printer or milling machine to manufacture the guide or splint and a pdf file with the planning information, images of each implant, the position thereof, client data, among others.

Once the surgical guide or splint 4 is prepared, the surgical process is started by the dental professional. After administering local anaesthesia, the disinfected guide or splint 4 should be seated firmly in the mouth. Once the guide 4 is placed on the dental quadrant where the implant 1 will be inserted, the specific sequence for the planned implant 1 or implants begins. The ring 4 is where the guided surgery milling cutter 40 will be supported and centred according to how the implantologist programmed the drilling process of the bone 50. The advantage over the known process is being able to use a single milling cutter 40 for implants with the same diameter and different lengths or in different depth positions, which has an effect on the kit or universal set of milling cutters 40, which will require fewer milling cutters compared to the kits of known procedures. Likewise, fewer carriers will also be necessary depending on the diameter and length or height of the implant.

Once the dental channel 13 has been drilled in the jawbone 50 where the implant 1 will be inserted, and with the help of the carrier 2, the implant 1 will be placed, adjusting it with a ratchet that acts on a free end 22 of the carrier and a screwdriver until said implant 1 is placed in the planned position inside the bone 50. The carrier 2 has a washer 21 as a mechanical stop that prevents it from being inserted beyond the ring 3 of the splint or guide 4, ensuring a correct position of the implant 1 in the previously planned location.

The carrier 2 is, as mentioned, an element to which the implant 1 is joined at a first end 23 and after inserting said first end 23 with the implant 1 into the hole 45 of the splint 4 up to the washer 21 of the carrier 2, at the end 22 opposite to the one joining 23 the implant 1, it abuts the ring 3 of the splint 4 after having applied tightening torque to the carrier 2. Said tightening torque for inserting the implant 1 into the bone 50 is applied to the carrier 2 above the washer 21 by means of a tightening tool or ratchet. The carrier 2 can even be used in applications of implants 1 below the bone 50 since the lower end 23 of the carrier 2 has a diameter less than or equal to the diameter of the head 11 of the implant 1, thus becoming an extension of the implant 1 and allowing it to be inserted into the bone 50 and therefore allowing the implant to be inserted and placed below the level of the bone 50 when necessary.

Once the implant 1 is placed in its position, the carrier 2 is removed from the implant 1. If necessary, an extractor can be used, making it possible to extract the carrier in a controlled manner and preventing movements in the implant 1 that has just been placed.

Figure 4:
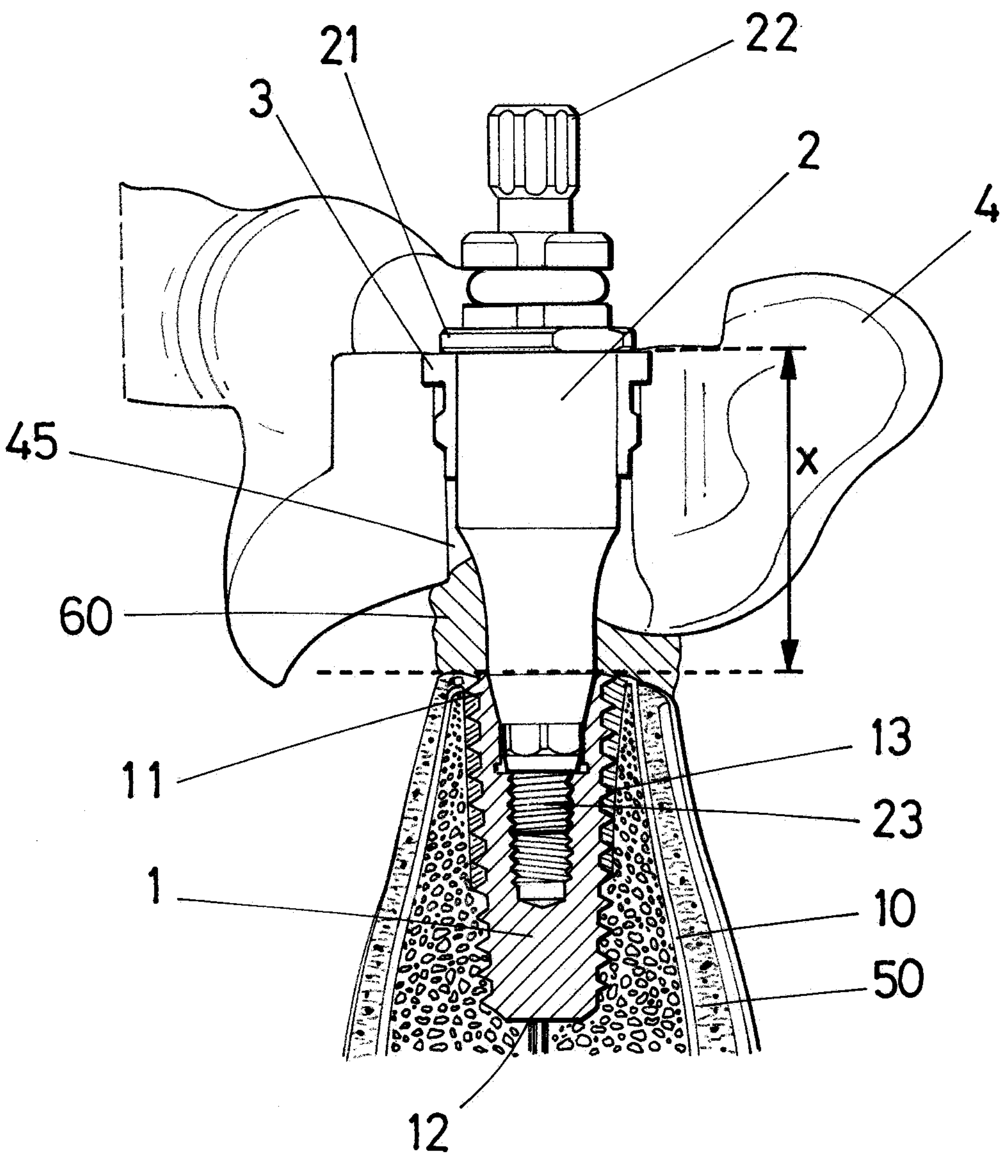
FIG. 4 shows a partial cross-sectional view of an assembly formed by a carrier (2), a ring (3), a splint (4) and an implant (1), among others.
Figure 5:
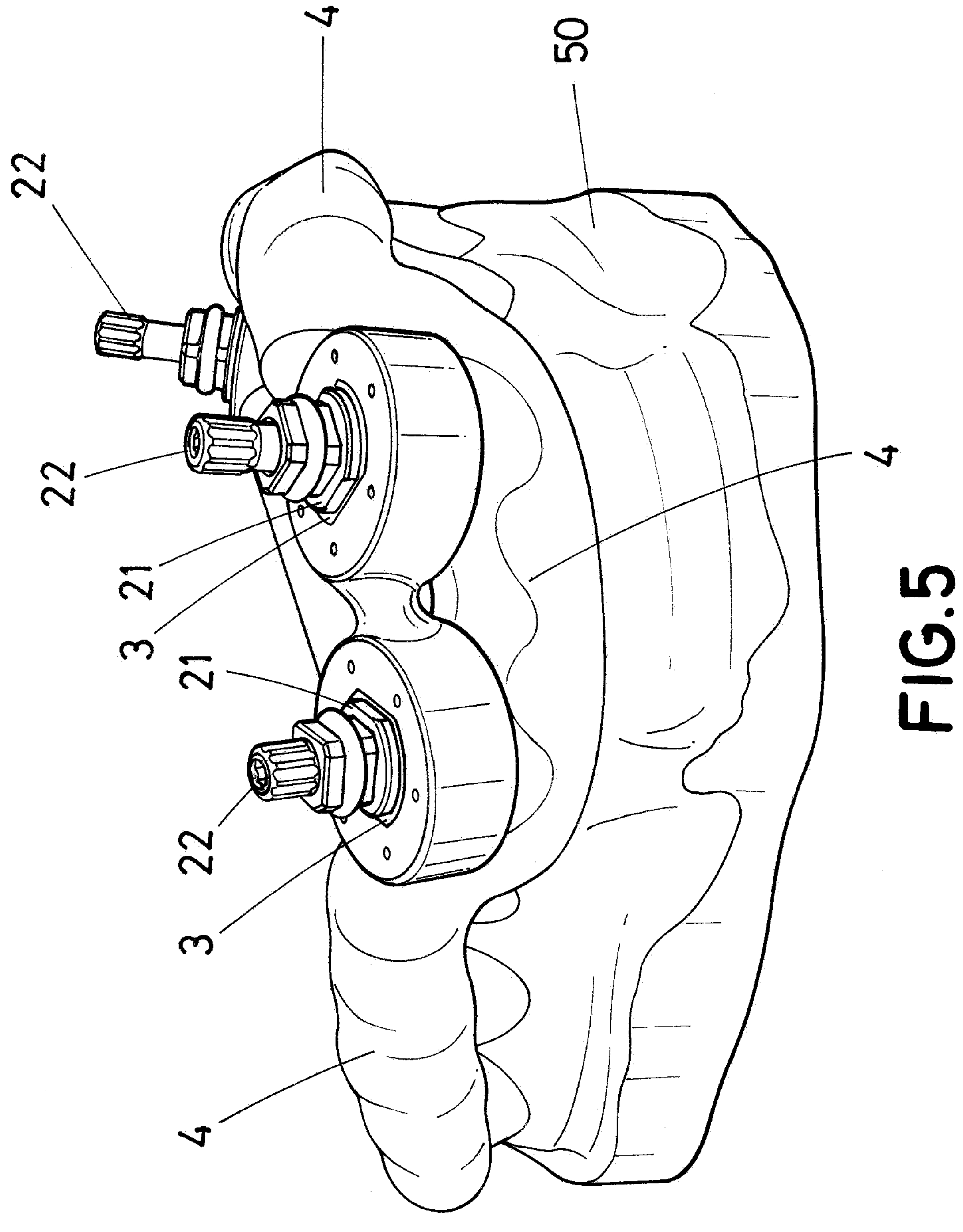
FIG. 5 shows a digital model of a splint or surgical guide with several carriers.

The new method makes it possible to determine the placement of the implants 1 at bone level (FIG. 1) and at different heights (FIG. 2) below the bone by means of correct planning and given the design of the carriers that have their end joining the implant with a diameter less than or equal to the diameter of the head 11 of the implant 1, as shown in FIG. 4.

The planning of the entire method can be determined through the libraries of the computer program, being able to simplify and use a single milling cutter for different implants, being able to position the height of the implant by means of different carriers with different heights which can vary the first distance X from 6 mm to 16 mm depending on the planning conditions.

The invention claimed is:

1. A method for manufacturing a splint/surgical guide (4) for implantation of at least one dental implant (1), comprising the following steps:

obtaining, by means of a scanning system and a computed tomography system, at least one three-dimensional image of a patient's oral cavity, to generate a digital oral model, determining features of the dental implant (1) to be implanted, including type, height and diameter of the dental implant (1), as well as location of a head of the at least said dental implant in the digital oral model, generating, based on the type and location of the at least one dental implant (1), a virtual surgical plan, which includes, at least:

creating a digital design of a surgical guide or splint (4) comprising at least one hole with a guide and stop ring (3), the stop ring located at a first distance from the location of the head (11) of the implant (1) in the digital oral model, choosing at least one milling tool (40) to be inserted into the hole of the splint (4), with a diameter sized based on the diameter of the implant (1), an inactive length (42) with a washer or protrusion (43) configured to come in contact with the guide and stop ring (3), and a machining length (41) ending at a free end (44), with the machining length (41) being greater than the height of the implant (1) and a distance between the washer or protrusion (43) and the free end (44) of the machining length (41) being equal to a sum of the first distance and the height of the implant, such that increasing or decreasing said first distance, varying a height of the splint (4) depending on the location of the head (11) of the implant (1), wherein the same at least one milling tool (40) can be used to machine different implant channels with the same diameter and different heights, determining the milling sequence by using the at least said milling tool (40) for machining the implant insertion channel in a jaw of the digital oral model, and manufacturing the splint or surgical guide (4) based on the digital design; and wherein the method comprises a further step for generating the virtual surgical plan, after determining the milling sequence, is determining a dental implant carrier with a specific diameter for insertion along with the implant into the hole of the splint for subsequent fastening in the implant insertion channel, said carrier being joined to the implant through a joining end having said end a diameter equal or less than that of the head of the implant, said carrier having a greater length than the first distance between the ring of the splint and the head of the implant.

2. The method, according to claim 1, wherein the surgical guide or splint comprises at least two holes with a ring in each of them, the rings being at two different first distances for the positioning of at least two implants with the same diameter.

3. The method, according to claim 2, wherein the milling tool for machining the at least two channels is the same.

4. A non-transitory computer-readable storage medium storing a program having code instructions that, when executed by a computer system or computer, carry out a method for generating a virtual surgical plan according to claim 1.

* * * * *